(12) United States Patent
Schmitt et al.

US007414147B2

(10) Patent No.: US 7,414,147 B2
(45) Date of Patent: Aug. 19, 2008

(54) METHOD FOR PRODUCING GLYCEROL CARBONATE METHACRYLATE

(75) Inventors: Bardo Schmitt, Mainz (DE); Maik Caspari, Alsbach-Haehnlein (DE)

(73) Assignee: Roehm GmbH & Co. KG, Darmstadt (DE)

( * ) Notice: Subject to any disclaimer, the term of this patent is extended or adjusted under 35 U.S.C. 154(b) by 49 days.

(21) Appl. No.: 10/580,840

(22) PCT Filed: Aug. 24, 2004

(86) PCT No.: PCT/EP2004/009423

§ 371 (c)(1),
(2), (4) Date: May 26, 2006

(87) PCT Pub. No.: WO2005/058862

PCT Pub. Date: Jun. 30, 2005

(65) Prior Publication Data

US 2007/0106044 A1    May 10, 2007

(30) Foreign Application Priority Data

Nov. 26, 2003  (DE)  ................ 103 55 830

(51) Int. Cl.
*C07D 317/36*  (2006.01)
*C08G 65/02*  (2006.01)
*C08L 67/00*  (2006.01)

(52) U.S. Cl. ..................................... 560/217
(58) Field of Classification Search ........... None
See application file for complete search history.

(56) References Cited

U.S. PATENT DOCUMENTS

| 2,979,514 | A | | 4/1961 | O'Brien et al. |
| 4,202,990 | A | | 5/1980 | Murakami et al. |
| 4,423,235 | A | | 12/1983 | Burgard et al. |
| 4,767,620 | A | * | 8/1988 | Mauz et al. ............. 525/54.1 |
| 4,772,666 | A | * | 9/1988 | Just et al. ............... 525/185 |
| 4,882,391 | A | | 11/1989 | Brindoepke et al. |
| 5,374,699 | A | | 12/1994 | Iwamura et al. |
| 6,936,734 | B2 | | 8/2005 | Schmitt et al. |
| 2004/0249191 | A1 | | 12/2004 | Schmitt et al. |

FOREIGN PATENT DOCUMENTS

| DE | 39 37 116 | 5/1991 |
| EP | 0 001 088 | 3/1979 |
| EP | 0 236 994 | 9/1987 |
| EP | 0 328 150 | 8/1989 |
| EP | 0 837 049 | 4/1998 |
| EP | 0 908 905 | 4/1999 |
| EP | 1 201 640 | 5/2002 |
| FR | 2 539 740 | 7/1984 |
| FR | 2 747 596 | 10/1997 |
| JP | 03 156803 | 7/1991 |
| JP | 2000 040526 | 2/2000 |
| JP | 2003 327854 | 11/2003 |
| WO | 03 022796 | 3/2003 |

\* cited by examiner

*Primary Examiner*—Yvonne Eyler
*Assistant Examiner*—Yevegeny Valenrod
(74) *Attorney, Agent, or Firm*—Oblon, Spivak, McClelland, Maier & Neustadt, P.C.

(57) ABSTRACT

The invention relates to a method for producing glycerol carbonate methacrylate in the presence of metal-chelate catalysts of the metal ion-1,3-diketonate type.

11 Claims, No Drawings

METHOD FOR PRODUCING GLYCEROL CARBONATE METHACRYLATE

The invention relates to a process for preparing glycerol carbonate methacrylate in the presence of metal chelate catalysts of the metal ion 1,3-diketonate type, especially zirconium acetylacetonate.

In the coatings industry (2-oxo-1,3-dioxolan-4-yl)-methyl methacrylate (glycerol carbonate methacrylate) is a much-used crosslinker. There are a variety of preparation processes known for glycerol carbonate methacrylate.

JP 2001018729 reacts glycerol carbonate with acryloyl chloride. The chloride wastes produced constitute a large environmental burden. WO 2000031195 reacts glycidyl methacrylate with $CO_2$. This process is carried out under high pressure. The apparatus needed for the process is intricate and expensive. DE 3937116 reacts a cyclocarbonate-containing alcohol with a carboxylic acid at elevated temperature and in the presence of an acidic catalyst. The desired product is obtained, after distillation, in a purity of 75.5%. The yield varies, as a function of the acid used, between 25.5% and 83%. With the purity achieved therein, of just 75.5%, there are numerous applications in which the product cannot be used.

It was an object of the invention to prepare glycerol carbonate methacrylate in high purity and with high yields.

This object has been achieved by a process for preparing (2-oxo-1,3-dioxolan-4-yl)methyl methacrylate in which methyl methacrylate is transesterified with glycerol carbonate in the presence of stabilizers and a metal chelate catalyst of the metal ion 1,3-diketonate type, especially zirconium acetylacetonate.

Surprisingly it has been found that through the use of zirconium acetylacetonate as a catalyst it is possible to operate under very mild conditions. The trans-esterification in the presence of zirconium acetyl-acetonate takes place at 50-80° C., preferably at 70° C.

Zirconium acetylacetonate is used preferably in amounts of 0.1-5.0% by weight, more preferably of from 1.0-3.0% by weight, based on the total weight of the batch.

As the catalyst it is possible, besides zirconium acetylacetonate, to use other metal 1,3-diketonates as well, such as lithium or zinc 1,3-diketonates, for example, or 1,3-diphenyl-propane-1,3-dione.

It has been found that through the reaction regime of the invention a low crosslinker content is obtained. The effect of a low crosslinker content in applications is that improved mechanical properties are obtained in the case of copolymerization with other monofunctional monomers. The material is less brittle. Crosslinkers observed include glycerol dimethacrylate and glycerol trimethacrylate. The amount of crosslinker observed in the product is preferably less than 5% by weight, more preferably less than 3% by weight.

Additionally it has been found that the product can be prepared with high yields and in high purity. Yields above 80% are obtained, with product purities of around 90%. The purities achieved mean that costly and inconvenient distillative purification is unnecessary. The monomer possesses a high boiling point and can therefore be separated off only in a high vacuum. Costly and intricate distillation apparatus, and the risk of polymerization under the high thermal load, which is frequently observed with this monomer, both disappear.

In the preparation of (2-oxo-1,3-dioxolan-4-yl)methyl methacrylate, stabilizers are added, which prevent free-radical polymerization of the (meth)acrylic groups during the reaction. These stabilizers are widely known in the art.

Use is made principally of 1,4-dihydroxybenzenes. Differently substituted dihydroxybenzenes, though, can also be employed. In general such stabilizers can be represented by the general formula (I)

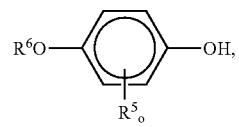

in which $R^5$ is a linear or branched alkyl radical having one to eight carbon atoms, halogen or aryl, preferably an alkyl radical having one to four carbon atoms, more preferably methyl, ethyl, n-propyl, isopropyl, n-butyl, isobutyl, sec-butyl, tert-butyl, Cl, F or Br;

o is an integer in the range from one to four, preferably one or two; and $R^6$ is hydrogen, a linear or branched alkyl radical having one to eight carbon atoms or aryl, preferably an alkyl radical having one to four carbon atoms, more preferably methyl, ethyl, n-propyl, isopropyl, n-butyl, isobutyl, sec-butyl or tert-butyl.

An alternative is to use compounds having 1,4-benzoquinone as their parent compound. Such compounds can be described by the formula (II)

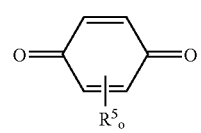

in which $R^5$ is a linear or branched alkyl radical having one to eight carbon atoms, halogen or aryl, preferably an alkyl radical having one to four carbon atoms, more preferably methyl, ethyl, n-propyl, isopropyl, n-butyl, isobutyl, sec-butyl, tert-butyl, Cl, F or Br; and o is an integer in the range from one to four, preferably one or two.

Also used are phenols of the general structure (III)

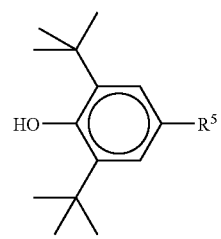

in which $R^5$ is a linear or branched alkyl radical having one to eight carbon atoms, aryl or aralkyl, propionic esters with mono- to tetrahydric alcohols, which may also contain heteroatoms such as S, O and N, preferably an alkyl radical having one to four carbon atoms, more preferably methyl, ethyl, n-propyl, isopropyl, n-butyl, isobutyl, sec-butyl or tert-butyl.

A further advantageous class of substance is represented by hindered phenols based on triazine derivatives of the formula (IV)

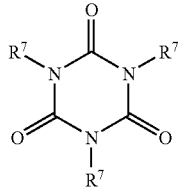

(IV)

where $R^7$=compound of the formula (V)

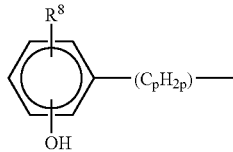

(V)

in which

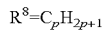

$R^8 = C_pH_{2p+1}$ where p=1 or 2.

Employed with particular success are the compounds 1,4-dihydroxybenzene, 4-methoxyphenol, 2,5-dichloro-3,6-dihydroxy-1,4-benzoquinone, 1,3,5-trimethyl-2,4,6-tris(3,5-di-tert-butyl-4-hydroxybenzyl)benzene, 2,6-di-tert-butyl-4-methylphenol, 2,4-dimethyl-6-tert-butyl-phenol, 2,2-bis[3,5-bis(1,1-dimethylethyl)-4-hydroxy-phenyl-1-oxopropoxymethyl)]1,3-propanediyl ester, 2,2'-thiodiethyl bis[3-(3,5-di-tert-butyl-4-hydroxy-phenyl)]propionate, octadecyl-3-(3,5-di-tert-butyl-4-hydroxyphenyl)propionate, 3,5-bis(1,1-dimethylethyl-2,2-methylenebis(4-methyl-6-tert-butyl)phenol, tris (4-tert-butyl-3-hydroxy-2,6-dimethylbenzyl)-s-triazine-2,4,6-(1H,3H,5H)trione, tris (3,5-di-tert-butyl-4-hydroxy)-s-triazine-2,46-(1H,3H,5H) trione or tert-butyl-3,5-dihydroxybenzene, more preferably 4-hydroxy-2,2,6,6-tetramethylpiperidinooxyl, hydroquinone, 4-methyl-2,6-di-tert-butylphenol, hydroquinone mono-methyl ether, 2-tert-butyl-6-(3-tert-butyl-2-hydroxy-5-methylbenzyl)-4-methylphenyl acrylate, 4-(methacryloyloxy)-2,2,6,6-tetramethylpiperidine-1-oxyl or 2,5-di-tert-butylhydroquinone.

For the purposes of the invention a tocopherol compound is used to stabilize ethylenically unsaturated monomers.

The tocopherol compounds which can be used in the context of the invention are chroman-6-ols (3,4-di-hydro-2H-1-benzopyran-6-ols) which are substituted in position 2 by a 4,8,12-trimethyltridecyl radical. The tocopherols which can be used with preference in accordance with the invention include alpha-tocopherol, beta-tocopherol, gamma-tocopherol, delta-tocopherol, zeta2-tocopherol, and eta-tocopherol, all of the aforementioned compounds each in the (2R,4'R,8'R) form, and also alpha-tocopherol in the (all-rac) form. Preference is given to alpha-tocopherol in the (2R, 4'R,8'R) form (trivial name: RRR-alpha-tocopherol), and also to the synthetic racemic alpha-tocopherol (all-rac-alpha-tocopherol). Of these, in turn, the latter is of particular interest owing to the relatively low price.

Based on the weight of the reaction mixture as a whole, the fraction of the stabilizers, individually or as a mixture, is generally 0.01%-0.50% by weight, the stabilizer concentration being selected preferably so as not to be detrimental to the color number in accordance with DIN 55945. Many of these stabilizers are available commercially.

Glycerol carbonate methacrylate can be used as a functional monomer in copolymers of coating materials and adhesives, and allows a subsequent, polymer-analogous reaction, including crosslinking with difunctional amines in a coating formulation. Furthermore, it can be used in battery electrolytes, in extrusion resins, and for metal extraction.

The examples given below are given in order better to illustrate the present invention, but have no capacity to restrict the invention to the features disclosed herein.

EXAMPLES

Example 1

118 g (1.0 mol) of glycerol carbonate are heated with 600 g (6.0 mol) of methyl methacrylate and 0.14 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 18.0 g of zirconium acetylacetonate and the amount of methyl methacrylate equivalent to the azeotrope distillate are added to the mixture. The mixture is heated to boiling. Alcoholysis is commenced at an overhead temperature of 70° C. Toward the end of the reaction it increased to 100° C.

After the end of the alcoholysis the mixture is cooled and the zirconium acetylacetonate catalyst is precipitated with dilute phosphoric acid. The suspension is then passed through a pressure filter and the filtrate is separated off.

For the purpose of separating off the glycerol carbonate, the filtrate is shaken in a separating funnel containing a dilute NaCl solution. The filtrate is degassed on a rotary evaporator at 70° C. and 200-10 mbar.

The yield is 80.6%. The purity of the product is 91.4%.

Experiment number: B1

Example 2

236 g (2.0 mol) of glycerol carbonate are heated with 1200 g (12.0 mol) of methyl methacrylate and 0.29 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 28.7 g of zirconium acetylacetonate and the amount of methyl methacrylate equivalent to the azeotrope distillate are added to the mixture. The mixture is heated to boiling. Alcoholysis is commenced at an overhead temperature of 70° C. Toward the end of the reaction it increased to 100° C.

After the end of the alcoholysis the mixture is cooled and the zirconium acetylacetonate catalyst is precipitated with dilute phosphoric acid. The suspension is then passed through a pressure filter and the filtrate is separated off.

For the purpose of separating off the glycerol carbonate, the filtrate is shaken in a separating funnel containing a dilute NaCl solution. The filtrate is degassed on a rotary evaporator at 70° C. and 200-10 mbar.

The yield is 87.4%. The purity of the product is 89.7%.

Experiment number: B2

Comparative Example 1

Isopropyl Titanate 236 g (2.0 mol) of glycerol carbonate are heated with 600 g (6.0 mol) of methyl methacrylate and 0.14 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 8.4 g of isopropyl titanate and the amount of methyl methacrylate equivalent to the azeotrope distillate are added to the mixture. The mixture is heated to boiling. Alcoholysis is commenced at an overhead temperature of 70° C. The reaction, however, is very sluggish, and is therefore terminated after 3 hours, with excess methyl methacrylate (MMA) being removed by distillation. The crude ester is analyzed.

Experiment number: C1

Comparative Example 2

Dioctyltin Oxide 118 g (1.0 mol) of glycerol carbonate are heated with 600 g (6.0 mol) of methyl methacrylate and 0.14 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 14.4 g of dioctyltin oxide and the amount of methyl methacrylate equivalent to the azeotrope distillate are added to the mixture. The mixture is heated to boiling. However, the reaction does not start, no methanol is formed, and the experiment is terminated.

Experiment number: C2

Comparative Example 3

LiOH/CaO 118 g (1.0 mol) of glycerol carbonate are heated with 600 g (6.0 mol) of methyl methacrylate and 0.14 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 4.0 g of LiOH, 10.4 g of CaO, and the amount of methyl methacrylate equivalent to the azeotrope distillate are added to the mixture. The mixture is heated to boiling. Alcoholysis is commenced at an overhead temperature of 70° C. Toward the end of the reaction it increased to 100° C.

Subsequently the batch is cooled and passed through a pressure filter, and the filtrate is separated off. For the purpose of separating off the glycerol carbonate, the filtrate is shaken in a separating funnel containing a dilute NaCl solution. The filtrate is degassed on a rotary evaporator at 70° C. and 200-10 mbar.

The yield is 79.6%. The purity of the product is 52.7%.

Experiment number: C3

Comparative Example 4

Lithium Methoxide 118 g (1.0 mol) of glycerol carbonate are heated with 600 g (6.0 mol) of methyl methacrylate and 0.14 g of 4-hydroxy-2,2,6,6-tetramethylpiperidinooxyl (Tempol) in a round-bottomed flask with distillation apparatus. Any water present is distilled off azeotropically with methyl methacrylate. The mixture is then cooled slightly. 14.4 g of lithium methoxide and the amount of methyl methacrylate equivalent to the azeotrope distillate are added to the mixture. The mixture is heated to boiling. Alcoholysis is commenced at an overhead temperature of 70° C. Toward the end of the reaction it increased to 100° C. After the end of the reaction, excess MMA is removed by distillation. The crude ester is filtered and then analyzed.

Experiment number: C4

The results of the experiments are summarized in the table below:

| Experiment | Catalyst Amount based on batch in % | Crude ester (containing MMA) | | | | | Monomer pure GC:* | | | | |
| --- | --- | --- | --- | --- | --- | --- | --- | --- | --- | --- | --- |
| | | Alcohol area % | Product area % | HS1 area % | HS2 area % | Polytest in MeOH | Yield % of th. | Alcohol area % | Product area % | HS1 area % | HS2 area % |
| B1 | Zirconium acetylacetonate 2.5 | 8.2 | 70.1 | 0.8 | 0.6 | clear | 80.6 | 0.9 | 91.4 | 0.9 | 0.9 |
| B2 | Zirconium acetylacetonate 2.0 | 8.1 | 72.7 | 0.9 | 0.9 | clear | 87.4 | 0.8 | 89.7 | 1.0 | 1.3 |
| C1 | Isopropyl titanate 1.0 | 90.7 | 6.5 | n.d. | n.d. | n.d. | n.d. | n.d. | n.d. | n.d. | n.d. |
| C2 | Dioctyltin oxide# 2.0 | n.d. | n.d. | n.d. | n.d. | n.d. | n.d. | n.d. | n.d. | n.d. | n.d. |
| C3 | LiOH/CaO 2.0 | 7.5 | 49.5 | 12 | 25 | clear | 79.6 | 0.3 | 52.7 | 12.3 | 27.3 |
| C4 | Lithium methoxide 2.5 | 2.2 | 68.9 | 1.6 | 20 | n.d. | n.d. | n.d. | n.d. | n.d. | n.d. |

Key:
*GC: further peaks disregarded
HS1 glycerol dimethacrylate
HS2 glycerol trimethacrylate
no conversion
n.d. not determined

The invention claimed is:

1. A process for preparing (2-oxo-1,3-dioxolan-4-yl)methyl methacrylate, comprising:
   transesterifying methyl methacrylate with glycerol carbonate in the presence of stabilizers and a metal chelate catalyst of the metal ion 1,3-diketonate type,
   precipitating the catalyst, and
   separating off a filtrate.

2. The process for preparing (2-oxo-1,3-dioxolan-4-yl)methyl methacrylate, according to claim 1 wherein the metal chelate catalyst is zirconium acetylacetonate.

3. The process for preparing (2-oxo-1,3-dioxolan-4-yl)methyl methacrylate, according to claim 1 wherein the transesterifying methyl methacrylate with glycerol carbonate takes place at 50-80° C.

4. The process for preparing (2-oxo-1,3-dioxolan-4-yl)methyl methacrylate, according to claim 3, wherein the transesterifying methyl methacrylate with glycerol carbonate takes place at 70° C.

5. The process for preparing (2-oxo-1,3-dioxolan-4-yl)methyl methacrylate, according to claim 2 wherein zirconium acetylacetonate comprises 0.1-5.0% by weight, based on the total weight of the batch.

6. The process for preparing (2-oxo-1,3-dioxolan-4-yl)methyl methacrylate, according to claim 5 wherein zirconium acetylacetonate comprises 1.0-3.0% by weight, based on the total weight of the batch.

7. The process for preparing (2-oxo-1,3-dioxolan-4-yl)methyl methacrylate, according to claim 1 wherein an amount of crosslinker formed during the preparation is less than 5% by weight.

8. The process for preparing (2-oxo-1,3-dioxolan-4-yl)methyl methacrylate, according to claim 1 comprising stabilizers in amounts of 0.01-0.50% by weight.

9. The process for preparing (2-oxo-1,3-dioxolan-4-yl)methyl methacrylate, according to claim 7 wherein the amount of crosslinker formed during the preparation is less than 3% by weight.

10. The process according to claim 1, wherein the precipitating the catalyst comprises adding dilute phosphoric acid.

11. The process according to claim 1, wherein the separating off the filtrate comprises passing a suspension of a precipitated mixture through a pressure filter.

* * * * *